US009752994B2

(12) United States Patent
Kojima et al.

(10) Patent No.: US 9,752,994 B2
(45) Date of Patent: Sep. 5, 2017

(54) IMAGE PROCESSING DEVICE, METHOD FOR CONTROLLING SAME, PROGRAM, AND INSPECTION SYSTEM

(71) Applicant: OMRON Corporation, Kyoto-shi, Kyoto (JP)

(72) Inventors: Takeshi Kojima, Kyoto (JP); Yasumoto Mori, Joyo (JP); Yasuhiro Ohnishi, Kyotanabe (JP)

(73) Assignee: OMRON Corporation, Kyoto-shi (JP)

( * ) Notice: Subject to any disclaimer, the term of this patent is extended or adjusted under 35 U.S.C. 154(b) by 565 days.

(21) Appl. No.: 14/475,603

(22) Filed: Sep. 3, 2014

(65) Prior Publication Data

US 2014/0372075 A1 Dec. 18, 2014

Related U.S. Application Data

(63) Continuation of application No. PCT/JP2013/051589, filed on Jan. 25, 2013.

(30) Foreign Application Priority Data

Mar. 8, 2012 (JP) ................................. 2012-051962

(51) Int. Cl.
*G01N 21/00* (2006.01)
*G01N 21/956* (2006.01)
(Continued)

(52) U.S. Cl.
CPC ........... *G01N 21/956* (2013.01); *G01B 11/00* (2013.01); *G01B 11/25* (2013.01); *G01B 11/254* (2013.01); *G01N 21/4738* (2013.01); *G01N 21/55* (2013.01); *G01N 21/8803* (2013.01); *G01N 21/8851* (2013.01); *G01N 21/95684* (2013.01);
(Continued)

(58) Field of Classification Search
CPC ............. G01N 21/956; G01N 21/9501; G01N 2021/95638; G01N 2021/95646; G06T 2207/30141; G06T 2207/30152; G06T 7/0002; G06T 7/586; H05K 1/0269
USPC ................... 356/237.1–237.5; 382/154, 203; 348/135
See application file for complete search history.

(56) References Cited

U.S. PATENT DOCUMENTS 7,724,379 B2 * 5/2010 Kawasaki .......... G01B 11/2509
356/603
8,334,985 B2 * 12/2012 Sho .................... G01B 11/2509
356/601
(Continued)

FOREIGN PATENT DOCUMENTS

JP 2009-128345 A 6/2009
JP 2011-232087 A 11/2011

OTHER PUBLICATIONS

International Search Report issued on Mar. 19, 2013.

*Primary Examiner* — Hoa Pham
(74) *Attorney, Agent, or Firm* — Mots Law, PLLC

(57) ABSTRACT

A measurement target is captured using two types of illumination patterns set such that only color features of specular objects change, the two images that are obtained are compared, and objects are identified as being specular objects or diffuse objects depending on whether the color features change markedly. At this time, the emission intensity distribution of each illumination pattern is devised such that specular lobe components that are included in reflected light are canceled out.

13 Claims, 9 Drawing Sheets

(51) Int. Cl.
  *G01B 11/00* (2006.01)
  *G01B 11/25* (2006.01)
  *G01N 21/47* (2006.01)
  *G01N 21/55* (2014.01)
  *G01N 21/88* (2006.01)

(52) U.S. Cl.
  CPC .......... *G01N 2021/557* (2013.01); *G01N 2021/95638* (2013.01); *G01N 2021/95646* (2013.01); *G01N 2021/95661* (2013.01); *G01N 2021/95669* (2013.01); *G01N 2201/062* (2013.01); *G01N 2201/12* (2013.01)

(56) References Cited

U.S. PATENT DOCUMENTS

| | | | |
|---|---|---|---|
| 8,363,929 B2* | 1/2013 | Kojima | G01B 11/2509 348/135 |
| 9,091,725 B2* | 7/2015 | Jeong | G01B 11/2531 |
| 2010/0295941 A1* | 11/2010 | Jeong | G01B 11/2531 348/135 |
| 2011/0002527 A1* | 1/2011 | Jeong | G01B 11/2531 382/141 |
| 2015/0253129 A1* | 9/2015 | Ohnishi | G01B 11/24 348/87 |

* cited by examiner

FIG. 2
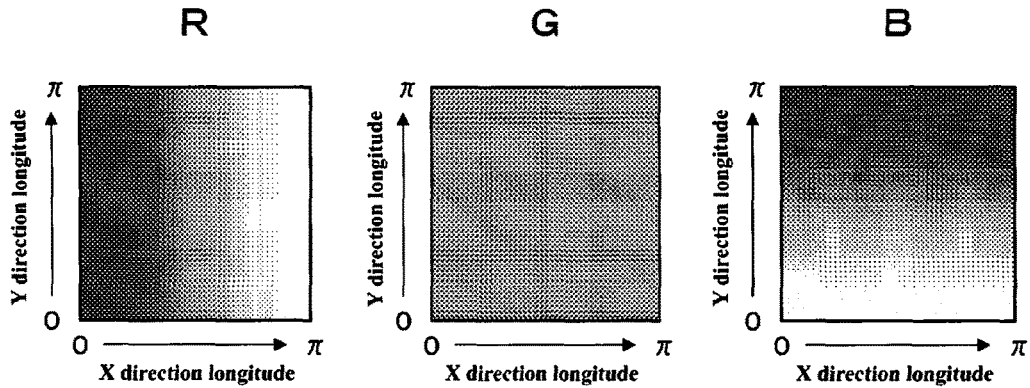
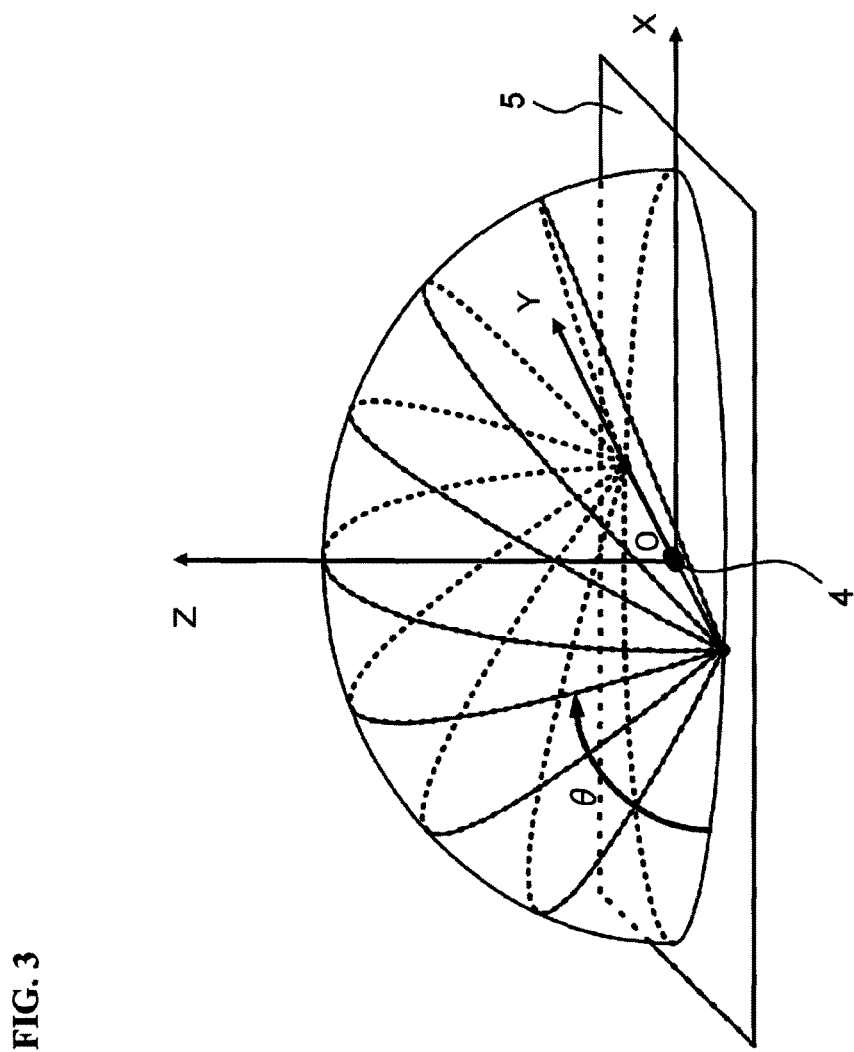
FIG. 3

(A)

(B)

IMAGE PROCESSING DEVICE, METHOD FOR CONTROLLING SAME, PROGRAM, AND INSPECTION SYSTEM

CROSS REFERENCE TO RELATED APPLICATIONS

This application claims priority to Japanese Patent Application No. 2012-051962 filed on Mar. 8, 2012, the entire contents of which are incorporated by reference herein.

TECHNICAL FIELD

The present invention relates to a technology for separating an image of a measurement target into specular object regions and diffuse object regions.

RELATED ART

Visual inspection devices that perform various types of inspection on a measurement target by capturing the measurement target with a camera and analyzing obtained images are known. With this type of inspection device, the processing algorithm may need to be changed, depending on whether the surface of the measurement target has specular reflection characteristics or diffuse reflection characteristics. This is because the reflected light of light from a specular direction is mainly observed in the case of an object that reflects light specularly (called a specular object), whereas incident light from various directions is mixed together in the case of an object that reflects light diffusely (called a diffuse object), resulting in the image information that is obtained being completely different between the specular object and the diffuse object. Accordingly, in the case where the measurement target is a printed circuit board or the like that has both diffuse objects (board surface, component bodies, resists, etc.) and specular objects (solder, lands, component electrodes, printed wiring, metal components, etc.), preprocessing for dividing up the image of the measurement target into specular object regions and diffuse object regions is performed prior to the inspection processing.

Patent Document 1 discloses a known technique for recognizing specular object regions from an image. With the technique disclosed in Patent Document 1, a so-called board visual inspection device employing a color highlight system, in which the gradient of the object surface (direction of the normal) is estimated by irradiating the board with R, G and B light at different angles of incidence from three ring-shaped illumination parts and observing the colors of the object surface, acquires an image when the illumination is arranged in the order RGB and an image when the illumination is arranged in the order BGR, and recognizes regions where there is a large color difference between these images as specular objects.

RELATED ART DOCUMENTS

Patent Documents

Patent Document 1: JP 2009-128345A

SUMMARY OF THE INVENTION

The technique of Patent Document 1 mentioned above is able to accurately recognize specular objects that have reflection characteristics approaching a perfect mirror surface. However, if the object surface is rough as in the case of lead-free solder, for example, there is a problem in that recognition accuracy decreases. The reason for this is shown in FIG. 12.

As shown in FIG. 12(A), in the case of an object with a perfect mirror surface, incident light is reflected only in the specular direction, and the reflected light is pointed and narrow (called a specular spike). Because the only light observed by the camera in this case is the reflected light of light incident from the specular direction of the optical axis of the camera, pure R, G or B color appears in the image. Thus, the color of the image changes greatly when the order of R, G and B is rearranged, enabling specular objects to be identified relatively easily.

In contrast, in the case of a specular object that does not have a perfect mirror surface, the reflected light will be constituted by a specular spike and light that spreads faintly in directions shifted slightly from the specular direction (this light is called specular lobe), as shown in FIG. 12(B). Specular lobe is the spreading of reflected light that is caused by minute unevenness (microfacets) on the object surface, with the specular lobe widening as the surface becomes rougher (i.e., as the orientation of the microfacets becomes more varied), and conversely narrowing and approaching the state of a perfect mirror surface as the surface becomes smoother. The light that is observed by the camera in this case is a mixture of the specular spike component of light incident from the specular direction of the optical axis of the camera and the specular lobe components of light incident from directions slightly shifted from the specular direction. Accordingly, the image of a specular object with a rough surface will be a mixture of R, G and B (e.g., gray). Therefore, there is little change in color even when the order of R, G and B is rearranged, making specular objects difficult to identify.

One aspect of the present invention was made in order to solve the above problems, and one aspect of the invention provides a technology that enables an image of a measurement target to be accurately separated into specular object regions and diffuse object regions, irrespective of the reflection characteristics of specular objects.

Means for Solving the Problems

In order to achieve the above object, the present invention is directed to imaging a measurement target with two types of illumination patterns in which the emission intensity distribution has been devised such that specular lobe components included in reflected light are canceled out, and recognizing specular object regions on the measurement target based on a result of comparing the two images that are obtained.

Specifically, an image processing device according to the present invention includes an illumination unit having a surface light source for irradiating a measurement target including a specular object and a diffuse object with light of a predetermined illumination pattern, an illumination control unit that controls the illumination pattern of the illumination unit, an imaging unit that images the measurement target, and a region recognition unit that recognizes a specular object region on the measurement target by analyzing an image obtained by the imaging unit, with the region recognition unit comparing a first image obtained by imaging the measurement target in a state where light of a first illumination pattern is irradiated from the illumination unit and a second image obtained by imaging the measurement target in a state where light of a second illumination pattern is irradiated from the illumination unit, and recognizing the specular object region on the measurement target based on a result of the comparison. The first image and the second image are images that include a plurality of the same channels. Here, the first illumination pattern includes a plurality of first illumination sub-patterns that each corresponds to a different one of the plurality of channels, and that have mutually different emission intensity distributions, the emission intensity distribution of each first illumination sub-pattern has an emission intensity that is uniform in-plane, or has an emission intensity that changes linearly in accordance with an angle of incidence of light with respect to the measurement target when considered at a certain cross-section that includes an optical axis of the imaging unit, the second illumination pattern includes a plurality of second illumination sub-patterns that each corresponds to a different one of the plurality of channels, and that have mutually different emission intensity distributions, the emission intensity distribution of each second illumination sub-pattern has an emission intensity that is uniform in-plane, or has an emission intensity that changes linearly in accordance with an angle of incidence of light with respect to the measurement target when considered at a certain cross-section that includes the optical axis of the imaging unit, and each first illumination sub-pattern and second illumination sub-pattern corresponding to the same channel have mutually different emission intensity distributions.

In the case of a specular object, basically, luminance corresponding to the emission intensity of points on the light source that are located in the specular direction when viewed from the imaging unit is observed. In other words, the image of a specular object takes pixel values that are dependent on the emission intensity distribution of the illumination. Hence, by performing imaging using two types of patterns having different emission intensity distributions for each channel, two images in which the pixel values of specular object regions differ can be obtained. On the other hand, since the components of light incident from various directions are mixed together in the case of a diffuse object, the pixel values remain largely unchanged even when the emission intensity distribution is varied. Accordingly, by comparing the pixel values of the two images, it is possible to distinguish specular object regions and diffuse object regions.

Furthermore, in the present invention, the emission intensity distributions of illumination sub-patterns are set such that "emission intensity is uniform in-plane" or "emission intensity changes linearly in accordance with the angle of incidence of light with respect to the measurement target when considered at a certain cross-section that includes the optical axis of the imaging unit". Such emission intensity distributions have the effect of cancelling out specular lobe components that are included in reflected light (hereinafter called the "lobe cancelling effect"). Accordingly, even if a specular object has a rough surface, only luminance corresponding to the emission intensity of points on the light source that are located in the specular direction when viewed from the imaging unit (i.e., specular spike component) will be observed, the same as in the case of a perfect mirror surface. Therefore, according to the present invention, an image of the measurement target can be accurately separated into specular object regions and diffuse object regions, irrespective of the reflection characteristics of specular objects. Note that although the emission intensity distributions of illumination sub-patterns are ideally set such that "emission intensity changes linearly", realizing strict linearity may be difficult for structural or design-related reasons, or the like. In such cases, linearity need only be substantially realized. A lobe cancelling effect that is sufficient for practical purposes is still obtained. That is, the concept that "emission intensity changes linearly" in the present invention includes the case where "emission intensity changes substantially linearly".

Preferably a ratio of a total amount of light in-plane between the plurality first illumination sub-patterns constituting the first illumination pattern is equal to a ratio of the total amount of light in-plane between the plurality of second illumination sub-patterns constituting the second illumination pattern. Also, the sub-patterns are more favorably set such that each first illumination sub-pattern and second illumination sub-pattern corresponding to the same channel have total amounts of light in-plane that are equal to each other. By thus matching the ratios of the total amounts of light or matching the total amounts of light themselves, portions of diffuse objects can be accurately compared between the first image and the second image.

Preferably the emission intensity distribution of each first illumination sub-pattern and the emission intensity distribution of each second illumination sub-pattern are set so as to satisfy $$\{L11(q), \ldots, L1n(q)\} \neq \{L21(q), \ldots, L2n(q)\}$$

for all points q, where q is a point on the surface light source of the illumination unit, i is a channel (i=1, ..., n; n is an integer of 2 or more), $L1i(q)$ is the emission intensity at the point q of the first illumination sub-pattern corresponding to the channel i, and $L2i(q)$ is the emission intensity at the point q of the second illumination sub-pattern corresponding to the channel i. Because a difference in pixel values arises between the first image and the second image whatever the direction of the normal of specular objects, specular object regions can be accurately recognized.

Also, preferably the emission intensity distribution of each first illumination sub-pattern and the emission intensity distribution of each second illumination sub-pattern are set such that $$f1(L11(q)-L21(q)) + \ldots + fn(L1n(q)-L2n(q))$$

takes the same value for all points q, where q is a point on the surface light source of the illumination unit, i is a channel (i=1, ..., n; where n is an integer of 2 or more), $L1i(q)$ is the emission intensity at the point q of the first illumination sub-pattern corresponding to the channel i, $L2i(q)$ is the emission intensity at the point q of the second illumination sub-pattern corresponding to the channel i, and fi is a function determined in advance for each channel i. Because the degree of difference in pixel values between the first image and the second image will thereby be the same whatever the direction of the normal of specular objects, the setting of a threshold that is used when separating specular objects and diffuse objects is facilitated.

In a case such as the above where emission intensity distribution setting is used, preferably the region recognition unit derives a feature amount representing a difference of the first image and the second image relating to a point p using a value that is obtained by $$f1(V11(p)-V21(p)) + \ldots + fn(V1n(p)-V2n(p))$$

where p is a point on the measurement target, $V1i(p)$ is the value of the channel i of the pixel corresponding to the point p in the first image, and $V2i(p)$ is the value of the channel i of the pixel corresponding to the point p in the second image, and determines that a portion at the point p is a specular object if the feature amount is greater than a threshold. By defining the feature amount in this way, the feature amount takes the same value whatever the direction of the normal of specular objects, thus enabling objects to be distinguished as specular objects or diffuse objects with a single threshold, and greatly facilitating processing.

Furthermore, preferably the first illumination sub-pattern corresponding to a channel k (1≤k≤n) has an emission intensity that is uniform in-plane, and the region recognition unit takes a value that is obtained by dividing $$f1(V11(p)-V21(p))+ \ldots +fn(V1n(p)-V2n(p))$$

by a value of V1k(p) as the feature amount. Because a decrease in luminance due to the occurrence of specular lobe can be canceled out through normalization with V1k(p), a feature amount that is not dependent on surface roughness can be obtained, enabling the accuracy with which specular objects are recognized to be improved.

Preferably a three-dimensional measurement processing unit that computes a direction of a normal of a surface of the specular object on the measurement target by analyzing an image obtained by the imaging unit, and computes a three-dimensional shape of the surface of the specular object from a result of the direction computation is further included, and the first image is also used in calculating the three-dimensional shape by the three-dimensional measurement processing unit. Because the number of times imaging is performed can be reduced by thus utilizing the same image in both specular object recognition processing and three-dimensional measurement processing, an improvement in the throughput of visual inspection can be achieved.

Note that the present invention can also be specified as an image processing device that includes at least some of the above units, and as an inspection system that is provided with this image processing device. Also, the present invention can be specified as a method for controlling an image processing device or an inspection system that includes at least some of the above processing, and as a computer program for causing an image processing device or an inspection system to perform this method or a computer-readable storage medium that stores this computer program. The above processing or units can be freely combined to the extent that technical inconsistencies do not arise.

Effects of the Invention

According to the present invention, an image of the measurement target can be accurately separated into specular object regions and diffuse object regions, irrespective of the reflection characteristics of specular objects.

BRIEF DESCRIPTION OF THE DRAWINGS

FIG. 2 is a diagram showing an exemplary illumination pattern for use in three-dimensional measurement processing.

FIG. 3 is a perspective diagram schematically showing isochromatic lines (isoemissive intensity lines) in an emission intensity distribution of R.

EMBODIMENTS OF THE INVENTION

Hereinafter, preferred embodiments of the present invention will be described with reference to the drawings. An image processing device of the present embodiment recognizes specular object regions (separates specular object regions and diffuse object regions) by analyzing an image of a measurement target. This device is applicable to object recognition or segmentation in various types of automated measuring devices, automated inspection devices, robot vision, and the like. Hereinafter, description will be given, taking a visual inspection device (AOI system) that performs processing such as quality inspection of soldering and three-dimensional shape measurement of on-board components, solder and the like as an example.

Overall Configuration of Visual Inspection Device

Figure 1:
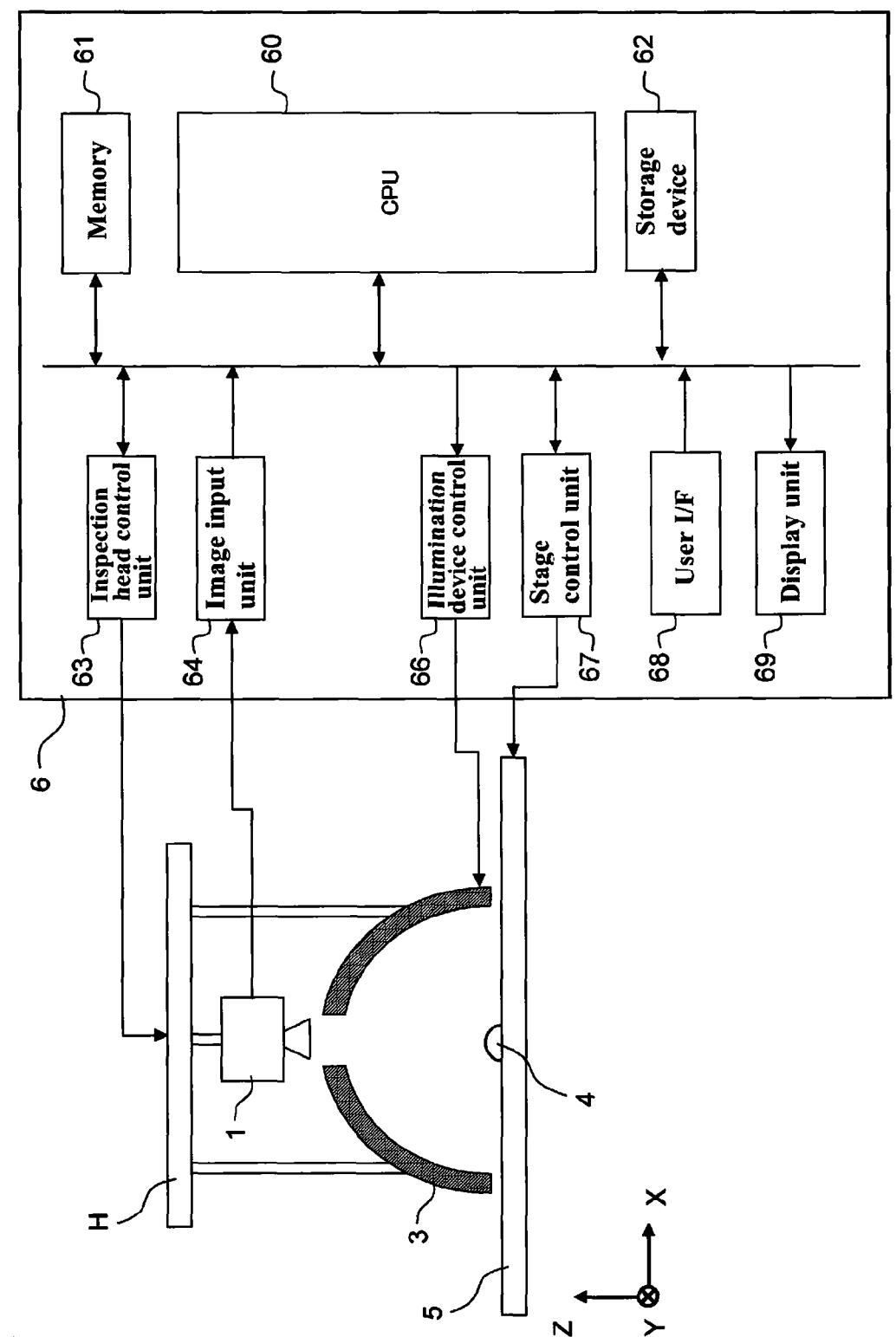
FIG. 1 is a diagram schematically showing a hardware configuration of a visual inspection device.

The overall configuration of the visual inspection device will be described with reference to FIG. 1. FIG. 1 is a diagram schematically showing a hardware configuration of the visual inspection device.

The visual inspection device is constituted so as to broadly include a measurement stage 5, an inspection head H, and an information processing device 6. An illumination device 3 for irradiating a measurement target 4 such as a printed circuit board or the like placed on the measurement stage 5 with measurement light, and a camera (image sensor) 1 that captures the measurement target 4 from vertically above are attached to the inspection head H. The information processing device 6 is provided with a CPU (central processing unit) 60, a memory 61, a storage device 62, an inspection head control unit 63, an image input unit 64, an illumination device control unit 66, a stage control unit 67, a user I/F 68, a display unit 69, and the like. The inspection head control unit 63 has a function of controlling movement of the inspection head H in a Z direction (direction perpendicular to the measurement stage 5), and the stage control unit 67 has a function of controlling movement of the measurement stage 5 in X and Y directions. The illumination device control unit 66 has a function of controlling on/off of the illumination device 3 (and switching of the illumination pattern when necessary). The image input unit 64 has a function of importing digital images from the camera 1. The user I/F 68 is an input device that is operated by a user, and corresponds to a pointing device, a touch panel, a keyboard, or the like, for example. The display unit 69 is a part in which measurement results and the like are displayed on screen, and includes a liquid crystal display or the like, for example.

The illumination device 3 is a surface light source having a dome shape, and the whole of this dome shape is an emission region. Note that an opening for the camera 1 is provided in an apex portion of the illumination device 3. Such an illumination device 3 can be constituted by, for example, a dome-shaped diffusion board and a plurality of LED chips arrayed on the back side of the diffusion board. The illumination device 3 can also be constituted by a display such as a liquid crystal display or an organic electroluminescence display that has been formed into a dome shape.

The emission region of the illumination device 3 preferably has a hemispherical dome shape so as to be able to irradiate the measurement target 4 with light from all directions. This enables measurement to be performed whatever direction the surface of the measurement target is facing. The surface light source may, however, take any shape, as long as the orientation of the surface of the measurement target is limited to a certain range. For example, if the orientation of the normal of the surface is limited to the substantially vertical direction, light does not need to be irradiated horizontally (from a direction with a shallow angle).

At the time of measurement, the inspection head H and the measurement stage 5 move relative to each other, and the measurement target 4 is positioned in a predetermined measurement position (in the example in FIG. 1, the center of the illumination device 3 (intersection of the optical axis of the camera 1 and the measurement stage 5)). The measurement target 4 is then captured in a state where measurement light of a predetermined illumination pattern is irradiated from the illumination device 3, and image data is imported into the information processing device 6 via the image input unit 64. At this time, a plurality of image data is acquired per measurement target 4 by performing image capture a plurality of times with different illumination patterns.

The visual inspection device of the present embodiment has a three-dimensional measurement processing function of measuring the three-dimensional shape of specular objects (solder, component electrodes, metal components, etc.) on a board by image analysis, in order to inspect the quality of the component placement on the board, the quality of soldering and the like with high accuracy. This function utilizes the reflection characteristics of specular objects, as will be discussed later, and thus cannot be applied to measurement of the three-dimensional shape of diffuse objects (e.g., board surface, component bodies, resists). Thus, with this device, preprocessing for recognizing/extracting specular object regions from an image of the measurement target 4 (specular object recognition processing) is performed before performing processing for computing three-dimensional shapes.

Hereinafter, the principles of three-dimensional measurement processing will be described initially to impart an understanding about the illumination patterns and lobe cancelling effect of the device, and then specular object recognition processing will be described, with this description being in reverse order to the actual order of processing.

Three-Dimensional Measurement Processing

In three-dimensional measurement processing, the measurement target 4 is captured using predetermined illumination patterns for three-dimensional measurement.

FIG. 2 shows an exemplary illumination pattern for three-dimensional measurement processing. In FIG. 2, the two-dimensional emission intensity distribution of the illumination device 3 which is a surface light source is schematically represented, with the horizontal axis showing longitude (from 0 to n) in the X direction, and the vertical axis showing longitude (from 0 to n) in the Y direction. Here, assuming that emission intensity takes a value from 0 to 255, the emission intensity 0 (darkest) is represented with black, the emission intensity 255 (brightest) is represented with white, and emission intensities in between are represented with gray.

The illumination patterns of the present embodiment are, as shown in FIG. 2, constituted by three illumination sub-patterns having mutually different emission intensity distributions, and each illumination sub-pattern corresponds to a different channel of an image. In other words, the value of reflected light that is observed when the first illumination sub-pattern is irradiated is the data of a first channel, the value of reflected light that is observed when the second illumination sub-pattern is irradiated is the data of a second channel, and the value of reflected light that is observed when the third illumination sub-pattern is irradiated is the data of a third channel.

The colors (spectrum distributions) of the light of the illumination sub-patterns may differ from each other or may be the same. Using light of different colors like R, G and B has the advantage of enabling an image for use in three-dimensional measurement to be acquired by performing illumination and imaging once, using a configuration that irradiates light obtained by combining these illumination sub-patterns and breaks down the light into its individual colors with a color filter provided in the camera. On the other hand, while processing takes slightly longer in the case where light of the same color is used since imaging needs to be performed a plurality of times with different illumination sub-patterns, there is an advantage in that measurement accuracy can be improved because of the stable amount of light that is illuminated due to the same light source being used. In the present embodiment, an example is described in which illumination sub-patterns of the three colors R, G and B are used. In this case, the image for use in three-dimensional measurement will be a RGB color image that includes three channels R, G and B.

As shown in FIG. 2, the illumination sub-pattern for R is set such that the emission intensity increases linearly from 50 to 250 in accordance with the longitude (0→π) in the X direction. In contrast, the illumination sub-pattern for G is set such that the emission intensity will be 150 for the entire in-plane region. Also, the illumination sub-pattern for B is set such that the emission intensity decreases linearly from 250 to 50 in accordance with the longitude (0→π) in the Y direction.

The emission intensity distribution of the illumination sub-pattern for R will be described in detail using FIG. 3. FIG. 3 is a perspective diagram schematically showing isochromatic lines (isoemissive intensity lines) in the emission intensity distribution of R. Here, the longitude in the X direction is represented with an angle $\theta$ about the Y-axis, when a point O where the measurement target 4 is placed on the measurement stage 5 is the origin. Points on the meridian of longitude $\theta$ are set to the same emission intensity $L(\theta)$. In the example in FIG. 2, $L(\theta)=50+(250-50)\times(\theta/\pi)$. Here, because the longitude $\theta$ corresponds to the angle of incidence of light on the measurement target 4 when considered at a cross-section (XZ cross-section) that includes the optical axis (Z-axis) of the camera 1 and the X-axis, it can be said that the emission intensity distribution of R, in the XZ cross-section, is set such that the emission intensity changes linearly in accordance with the angle of incidence of light. Although not illustrated, in the same way it can be said that the emission intensity distribution of B, in a YZ cross-section, is set such that the emission intensity distribution changes linearly in accordance with the angle of incidence of light.

In the case where illumination patterns set in this way are used, colors (combinations of the emission intensities of R, G and B) that differs for every position on the surface light source will be emitted. For example, at a position (X direction longitude, Y direction longitude)=(0, 0), (R, G, B)=(50, 150, 250), resulting in strong blueness, and at a position (X direction longitude, Y direction longitude)=(π/2, π/2) (i.e., zenith portion), (R, G, B)=(150, 150, 150), resulting in gray.

Figure 4:
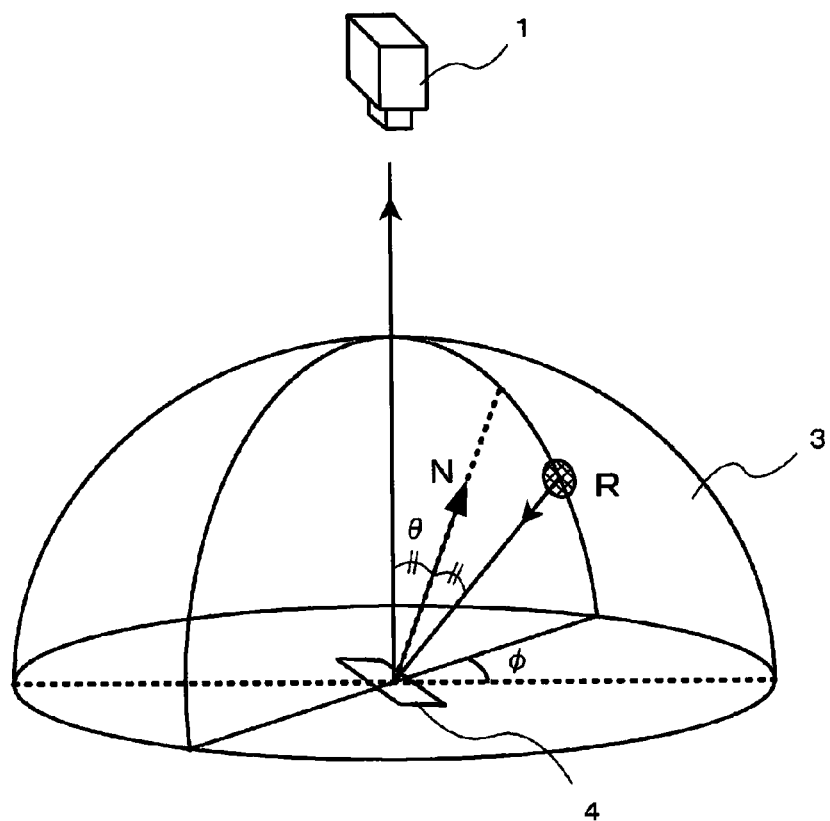
FIG. 4 is a diagram illustrating a correspondence between the direction of the normal of a measurement target and emission regions on a surface light source.

By using such illumination patterns, the surface shape (direction of the normal) of the measurement target can be measured with only one image. This will be described with reference to FIG. 4. The direction of the normal at a certain point on the surface of the measurement target 4 is given by the direction of an arrow N, with the zenith angle given as θ and the azimuth angle given as φ. In the case where the measurement target 4 is a specular object, the color of the point on the object that is captured with the camera 1 will be the reflected light of light that is emitted at a position R of the surface light source (illumination device 3) and incident on the measurement target 4. The direction (θ, φ) of the normal of the surface and the direction of incident light (position R on the surface light source) thus correspond one-to-one. Given that light that is incident from a different direction has a different color (different combination of the emission intensities of R, G and B), the direction of the normal at that point can be specified for both the zenith angle and the azimuth angle by investigating the color features of the pixels (combination of values for each channel). Note that the correspondence relationship between the color features of pixels and the direction of the normal can be provided in advance as a table. When the direction of the normal can be computed for each point (each pixel) of an image, the three-dimensional shape of a specular object can be restored by converting the normal of each point into a gradient and connecting the gradients.

Lobe Cancelling Effect

As mentioned above, with this device, the emission intensity distributions of R and B are set such that emission intensity changes linearly in accordance with the angle of incidence, and the emission intensity distribution of G is set so as to have a uniform intensity in-plane. Such emission intensity distributions have the effect of cancelling out specular lobe components that are included in reflected light (lobe cancelling effect), thus enabling similar color features to the case of a perfect mirror surface to be observed even with a specular object having a rough surface such as lead-free solder. Hereinafter, this lobe cancelling effect will be described.

Figure 12:
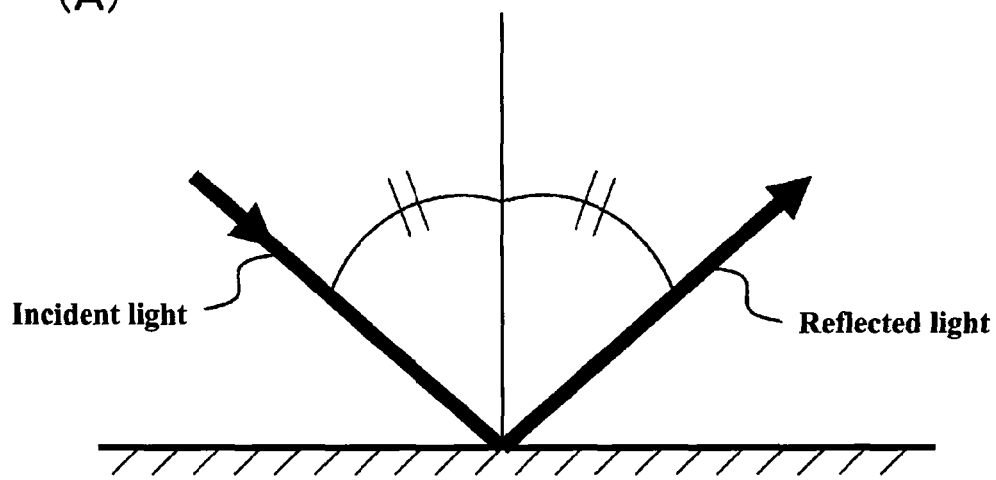
FIG. 12 is a diagram for illustrating reflection characteristics of a specular object.
Figure 12:
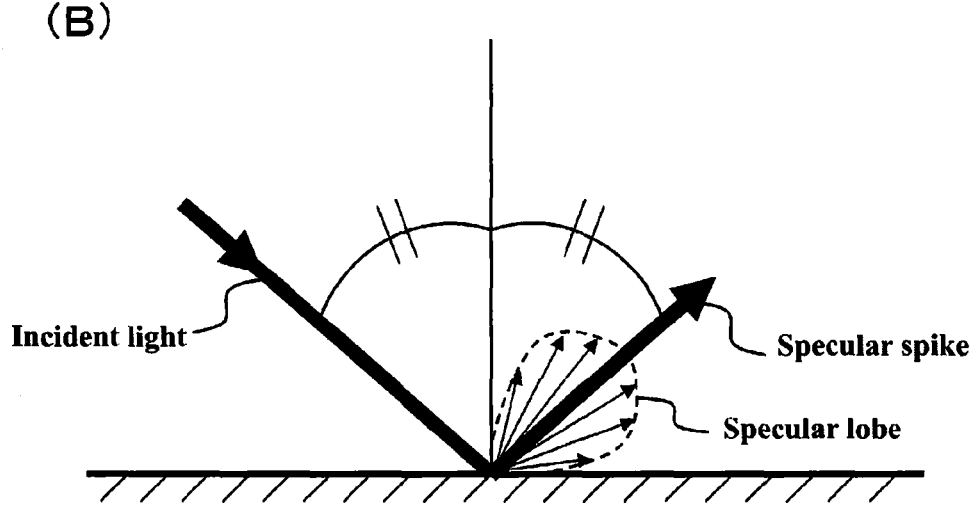

As shown in FIG. 12(B), in the case of a specular object that does not have a perfect mirror surface, specular lobe occurs in addition to specular reflection (specular spike). Thus, the light that is observed with the camera 1 will be light that results from the mixing of the specular lobe components of light incident from directions slightly shifted from the specular direction with the specular spike component of light incident from the specular direction of the optical axis of the camera 1. Accordingly, the color features will differ from those in the case of a perfect mirror surface.

If illumination can be performed at this time such that the components of light incident from directions other than the specular direction are exactly cancelled out and color features that are similar to those in the case of a perfect mirror surface are kept, even objects with rough surfaces or objects whose reflection characteristics are not uniform can be measured as though they where objects with a perfect mirror surface. This is realized, theoretically, by setting the emission intensity distribution of the illumination device 3 as follows.

Figure 5:
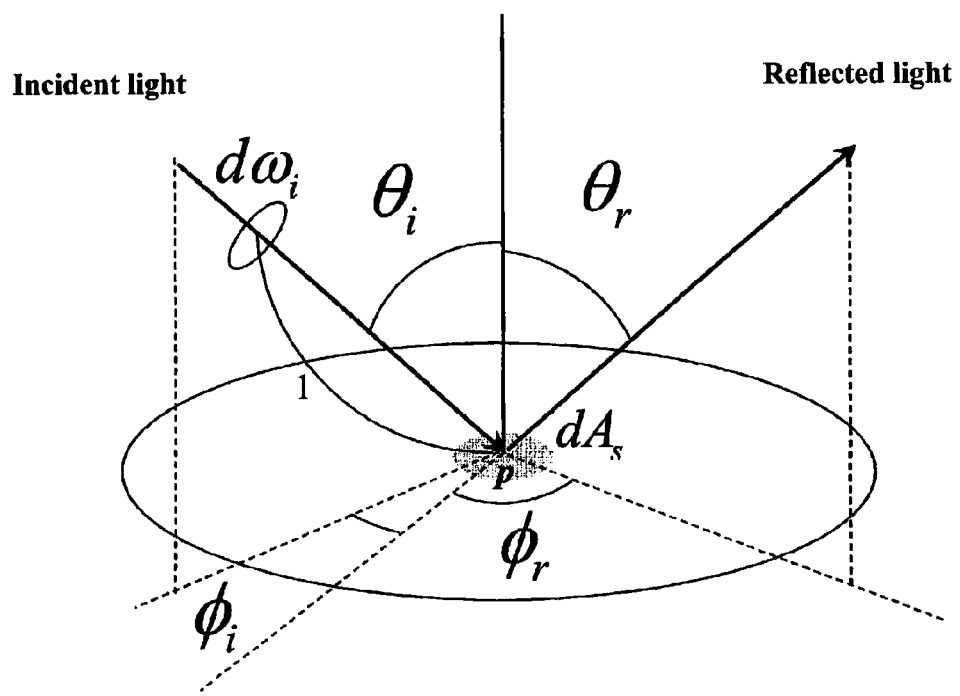
FIG. 5 is a diagram for illustrating incident light and reflected light.

That is, as shown in FIG. 5, when the light source distribution of light that is incident at a measurement point p from the direction of the angle of incidence (θi, φi) is given as Li (p, θi, φi), the following formula should hold for a given normal vector at the point p, and a given point symmetrical region Ω in the emission region.

$$\iint_{\Omega} L_i(p,\theta_i,\phi_i) \cdot f(p,\theta_i,\phi_i,\theta_r,\phi_r) \cos\theta_i \sin\theta_i d\theta_i d\phi_i = L_i(p, \theta_{is}, \phi_{is}+\pi)$$ Formula 1

Here, p is the measurement point on the object surface, (θi, φi) is the direction of incident light (where θ is the zenith angle component, and φ is the azimuth angle component; the same applies below), (θr, φr) is the direction of reflected light (camera direction), (θis, φis) is the specular direction relative to (θr, φr), f is the reflection characteristic of the point p, and Ω is the point symmetrical region centered on (θis, φis).

The emission intensity distributions of the illumination patterns (illumination sub-patterns) used in the present embodiment are all approximate solutions of the above formula.

Figure 6:
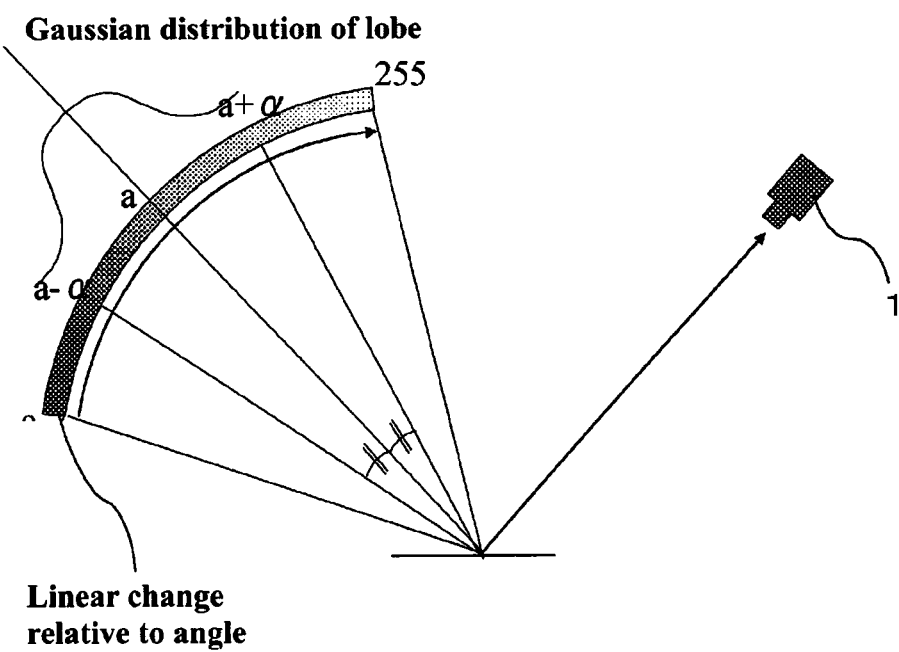
FIG. 6 is a diagram for illustrating a lobe cancelling effect.

The offsetting of the influence of specular lobe by using such illumination patterns will be now described from another viewpoint, with reference to FIG. 6. FIG. 6 shows the one dimensional direction of the luminance change direction that is obtained by light approaching the ideal, in order to describe the lobe cancelling effect of the illumination patterns in the present embodiment. Here, as shown in FIG. 6, only light from three points, namely, an angle a (specular direction), an angle a+α, and an angle a−α, is considered. The lobe coefficients of light from the positions of angles a+α and a−α are assumed to both be equal to σ. Also, the emission intensities of the illumination device 3 are given, proportionally to the angles, as (a−α)L, aL and (a+α)L at the respective positions of the angles a−α, a and a+α. The combination of the reflected light from these three points will thus be σ(a−α)L+aL+σ(a+α)L=(1+2σ)aL, and the influence due the specular lobe components of peripheral light is clearly offset. Note that although only the two points a±α are considered here, it should be readily obvious that the influence of the specular lobe components of peripheral light is completely offset. This holds for the respective light of R, G and B, and, accordingly, the color features that are represented by the ratio of the emission intensities of the colors RGB will be the same as those in the case of perfect specular reflection. Therefore, similar color features to those in the case of perfect specular reflection can be obtained, even if the object has a rough surface or reflection characteristics that are not uniform.

Note that the above description was given with regard to the direction in which the most ideal effects are obtained. With regard to other directions, the linearity described above breaks down, and the influence of the specular lobe components cannot strictly be offset, although it is possible to remove the influence of the specular lobe components in a range that is adequate for practical purposes.

Specular Object Recognition Processing

The three-dimensional measurement processing mentioned above utilizes the reflection characteristics of specular objects, and thus cannot be applied to three-dimensional measurement of diffuse objects. Hence, the device performs processing for specifying specular object regions in an image before executing processing for restoring three-dimensional shapes from the color features of the image. The basic algorithm of this processing involves capturing the measurement target using two types of illumination patterns set such that only the color features of specular objects change, comparing the two images that are obtained, and identifying objects as being specular objects or diffuse objects depending on whether the color features change markedly.

Setting Conditions of Illumination Patterns

Hereinafter, the setting conditions of two types of illumination patterns will be described. Note that the first of the illumination patterns is referred to as the "first illumination pattern", and the respective illumination sub-patterns constituting the first illumination pattern are referred to as the "first illumination sub-patterns", while the second of the illumination patterns is referred to as the "second illumination pattern", and the respective illumination sub-patterns constituting the second illumination pattern are referred to as the "second illumination sub-patterns". Also, the image obtained using the first illumination pattern is referred as the "first image" and the image obtained using the second illumination pattern is referred to as the "second image".

Condition 1: Each first illumination sub-pattern and second illumination sub-pattern corresponding to the same channel have mutually different emission intensity distributions.

In the case of a specular object, basically, the luminance corresponding to the emission intensity of points on the light source that are located in the specular direction as seen from the camera 1 is observed. In other words, the image of a specular object takes pixel values that are dependent on the emission intensity distribution of the illumination. On the other hand, in the case of a diffuse object, the components of light incident from various directions are mixed together, and thus the pixel values remain largely unchanged even when the emission intensity distribution is varied. Hence, by performing image capture using two types of illumination patterns that satisfy condition 1, two images having pixel values that differ only in specular object regions can be obtained.

Condition 2: Patterns of emission intensity distribution having the lobe cancelling effect are used for both the first illumination pattern and the second illumination pattern. That is, both the first illumination pattern (each of the first illumination sub-patterns) and the second illumination patterns (each of the second illumination sub-patterns) have an emission intensity distribution that is a solution or an approximate solution of the above formula (1).

As a result of the lobe cancelling effect, only luminance corresponding to the emission intensity of points on the light source that are located in the specular direction as seen from the camera 1 (i.e., specular spike component) will be observed, the same as in the case of a perfect mirror surface, even if the specular object has a rough surface. Therefore, by using illumination patterns that satisfy condition 2, it is possible to accurately separate specular object regions and diffuse object regions, irrespective of the reflection characteristics of specular objects.

The above two conditions are necessary conditions, but it is also preferable to set the emission intensity distribution to satisfy the following conditions.

Condition 3: The ratio of the total amount of light in-plane between the first illumination sub-patterns is equal to the ratio of the total amount of light in-plane between the second illumination sub-patterns.

Since components of light incident from various directions are mixed together in the reflected light from a diffuse object, the image of a diffuse object takes pixel values that are dependent on the total amount of light (in-plane integral of emission intensities) of the illumination. That is, the ratio of the total amounts of light in-plane between the plurality of illumination sub-patterns determines the color balance (hue) of the image of a diffuse object. Because the color balance of portions of a diffuse object will be the same between the first image and the second image if the ratio of the first illumination pattern and the ratio of the second illumination pattern are equalized, as mentioned above, the images can be accurately compared. Note that the pixel values themselves differ in the case where the total amount of light differs (brightness differs) between the first illumination pattern and the second illumination pattern even if the ratios are the same, in which case level adjustment for matching the values of both images can be performed before comparing the images.

Incidentally, although an image will be a color image in the case where the channels of the image are color channels such as R, G and B, an image is, strictly, not a color image in the case where the channels of the image represent luminance (unrelated to color), and thus it may not be appropriate to use terms such as "color" balance and "color" phase (hue). However, even in the case of the latter, the image can be treated in the same way as a color image as far as image processing is concerned when there are a plurality of channels (alternatively, such images can be treat as pseudo color images by artificially allocating a color to each channel), and thus no particular distinction is made between the two in this specification.

Condition 4: The total amount of light in-plane is equal between each first illumination sub-pattern and second illumination sub-pattern corresponding to the same channel.

If the total amounts of light coincide, the pixel values of the portions of the diffuse object will be substantially matched. Accordingly, because corresponding values of the same channels can be directly compared (without level adjustment, etc.), a difference image can be calculated simply by subtracting the values, for example.

Condition 5: $\{L11(q), \ldots, L1n(q)\} \neq \{L21(q), \ldots, L2n(q)\}$ holds for all points q on the surface light source of the illumination device 3. Here, i is the channel (i=1, ..., n; n is an integer of 2 or more), $L1i(q)$ is the emission intensity at point q in the first illumination sub-pattern corresponding to channel i, and $L2i(q)$ is the emission intensity at point q in the second illumination sub-pattern corresponding to channel i.

Condition 5 involves setting the emission intensity distribution of each illumination pattern such that the same color does not appear at the same point q on the surface light source between the first illumination pattern and the second illumination pattern. By satisfying condition 5, a difference in pixel values arises between the first image and the second image whatever the direction of the normal of specular objects, enabling specular object regions to be accurately recognized.

Condition 6: $f1(L11(q)-L21(q))+ \ldots +fn(L1n(q)-L2n(q))$ takes the same value for all points q on the surface light source of the illumination device 3. Here, fi is a function that is determined in advance for every channel i, and is for adjusting the balance of the difference in emission intensity between channels. For example, a given function can be used, such as a function (abs) for obtaining an absolute value, a function for multiplying by a constant, or a normalizing function. Note that the function fi is assumed to also include a function for multiplying by the constant 1 (function for not performing any operation).

Condition 6 involves the evaluation value taking the same value for all points q on the surface light source, in the case where the difference in emission intensity of the first illumination pattern and the second illumination pattern is evaluated using the above formula. Accordingly, by setting the illumination patterns such that condition 6 is satisfied, the degree of difference in pixel value between the first image and the second image will be the same whatever the direction of the normal of a specular object, thereby facilitating the setting of the threshold that is used when separating specular objects and diffuse objects.

Difference Feature Amount

Note that in the case where the illumination pattern is set to satisfy condition 6, it is favorable to derive a feature amount F representing the difference between the first image and the second image using the same function fi as that used in setting the illumination pattern, as in the following formula.

$$F = f1(V11(p) - V21(p)) + \ldots + fn(V1n(p) - V2n(p))$$

Here, p is a point on the measurement target, $V1i(p)$ is a value of the channel i of the pixel corresponding to the point p in the first image, and $V2i(p)$ is a value of the channel i of the pixel corresponding to the point p in the second image.

By thus defining the feature amount, the feature amount F takes the same value whatever the direction of the normal of the specular object, enabling objects to be distinguished as being specular objects or diffuse objects with a single threshold, and greatly facilitating processing.

Furthermore, it is even more favorable to define the value $(F/V1k(p))$ that results from dividing the value F obtained with the above formula by the value $(V1k(p))$ of the channel k of the pixel corresponding to the point p in the first image as the feature amount, after having set the first illumination sub-pattern corresponding to the channel k ($1 \le k \le n$) as an emission intensity distribution that is uniform in-plane.

While the intensity of reflected light decreases slightly due to the occurrence of specular lobe in the case of a specular object with a rough surface, the extent of this decrease depends on the roughness of the surface and is thus difficult to predict. The value $V1k(p)$ obtained using the pattern having a uniform emission intensity distribution in-plane takes a value that includes the decrease in intensity that is dependent on the surface roughness. Therefore, dividing the values of all the channels by this value $V1k(p)$ is equivalent to canceling out the decrease in intensity that is dependent on surface roughness, thereby enabling a feature amount that is not dependent on surface roughness to be obtained, and enabling the recognition accuracy of specular objects to be improved.

Working Example

An example of a first illumination pattern and a second illumination pattern created so as to satisfy the illumination pattern setting conditions mentioned above is shown in FIG. 7. Three first illumination sub-patterns constituting the first illumination pattern are shown in the upper half of FIG. 7, and three second illumination sub-patterns constituting the second illumination pattern are shown in the lower half.

Figure 7:
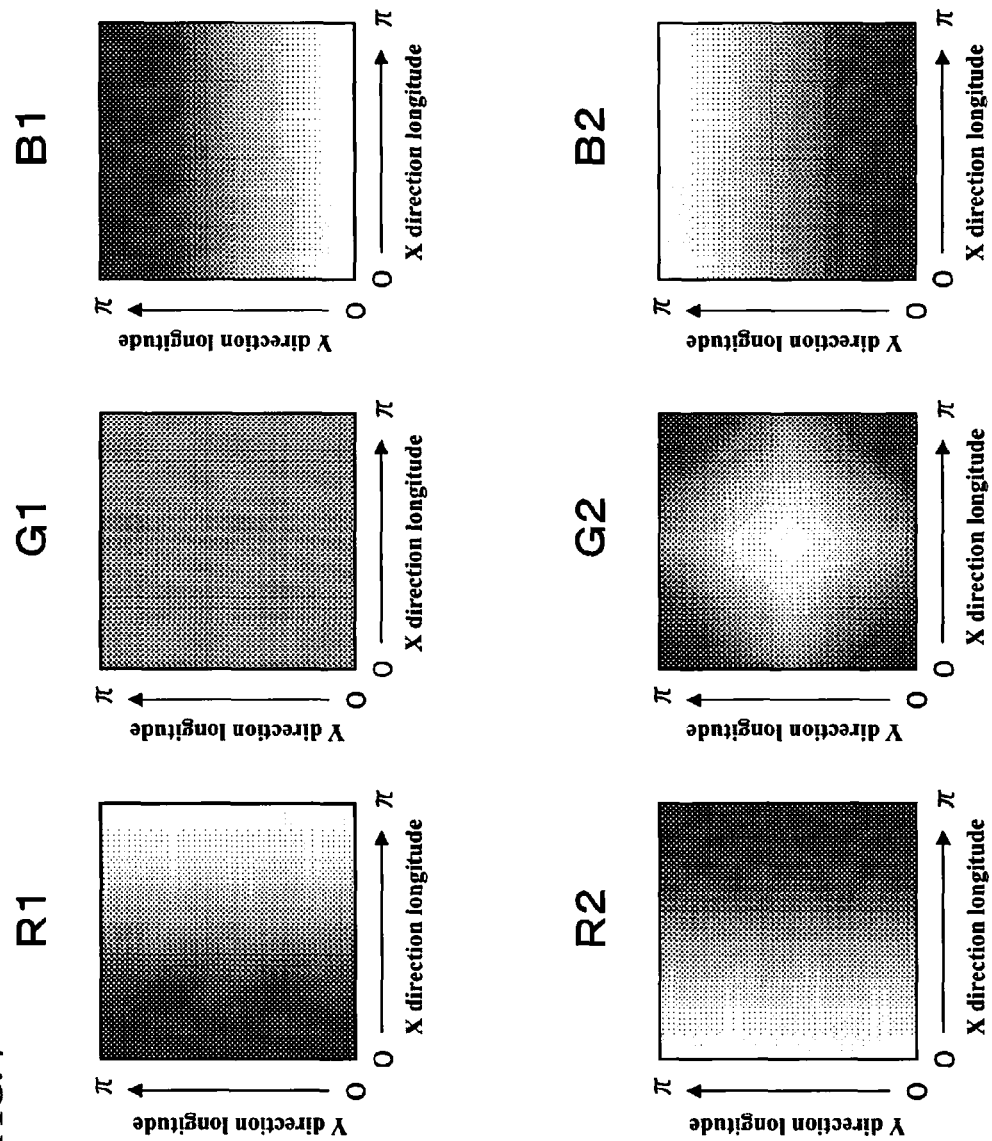
FIG. 7 is a diagram showing exemplary illumination patterns for use in specular object recognition processing.

In this working example, the same illumination pattern as used in three-dimensional measurement is used as the first illumination pattern. This is because the image acquired for use in three-dimensional measurement can also be appropriated for use in specular object recognition processing. The second illumination pattern in FIG. 7 is an illumination pattern designed to satisfy the above setting conditions when combined with the first illumination pattern.

Specifically, the second illumination sub-pattern of the R channel is the first illumination sub-pattern reversed in the X direction, and is set such that the emission intensity decreases linearly from 250 to 50 in accordance with the longitude (0→π) in the X direction. Also, the second illumination sub-pattern of the B channel is the first illumination sub-pattern reversed in the Y direction, and is set such that the emission intensity increases linearly from 50 to 250 in accordance with the longitude (0→π) in the Y direction. The second illumination sub-pattern of the G channel is set to satisfy the above condition 6, such that the value of the following formula takes the same value cnst for all points on the surface light source.

$$abs(R2-R1)/2 + (G2-G1) + abs(B2-B1)/2 = cnst$$

Here, R1, G1 and B1 are the emission intensities of the first illumination sub-patterns, and R2, G2 and B2 are the emission intensities of the second illumination sub-patterns. That is, in this working example, the function "multiply the absolute value of the difference by ½" is employed in the formula of condition 6 as f1 and f3, and the function "multiply by 1 (do not perform any operation)" is employed as f2.

Because G1 is 150 at all points and conditions 3 and 4 hold when cnst is 100, the emission intensity of the second illumination sub-pattern of the G channel is ultimately given by the following formula.

$$G2 = 250 - abs(R2-R1)/2 - abs(B2-B1)/2$$

This pattern forms a distribution in which the emission intensity takes the maximum value 250 when (X direction longitude, Y direction longitude)=(π/2, π/2), and the emission intensity decreases linearly toward the points (X direction longitude, Y direction longitude)=(0, 0), (π, 0), (0, π) and (π, π). The minimum value of the emission intensity is 50. With this emission intensity distribution, the emission intensity also changes linearly in accordance with the angle of incidence of light, when considered at a cross-section that includes the optical axis (Z-axis) of the camera and forms an angle π/2 (or −π/2) with the X-axis. Therefore, this pattern can also be said to have a lobe cancelling effect.

The first and second illumination patterns set as described above satisfy conditions 1 and 2. Furthermore, the total amounts of light of the first illumination sub-patterns are R:G:B=(250+50)/2:150:(250+50)/2=1:1:1, and the total amounts of light of the second illumination sub-patterns are also R:G:B=(250+50)/2:150:(250+50)=1:1:1, thus satisfying conditions 3 and 4. It is also clear from FIG. 7 that condition 5 is satisfied, and condition 6 is also satisfied given that G2 is determined as described above.

Figure 8:
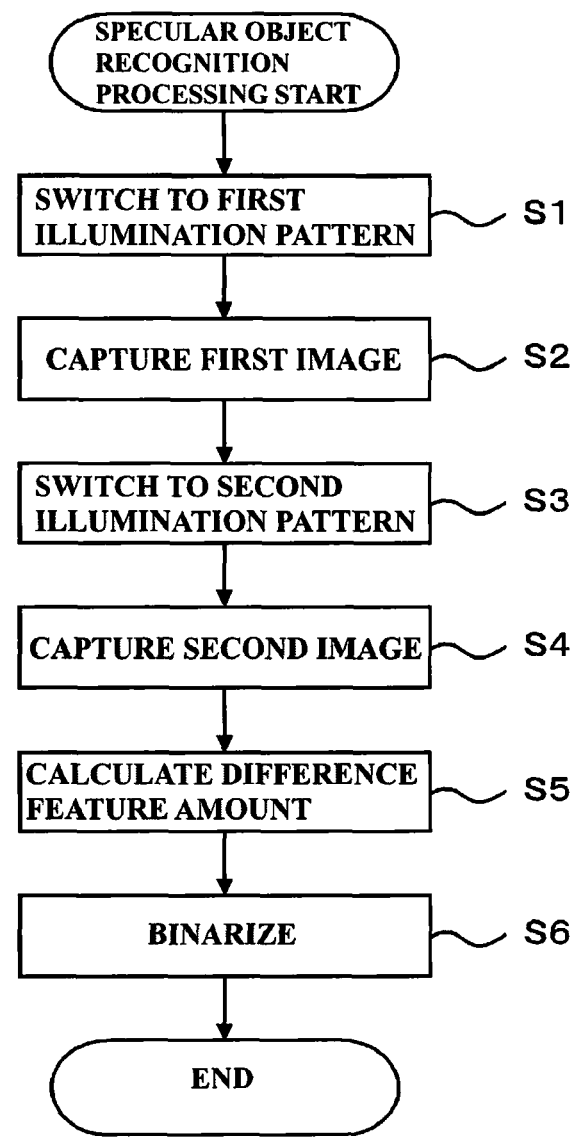
FIG. 8 is a flowchart of specular object recognition processing.
Figure 9:
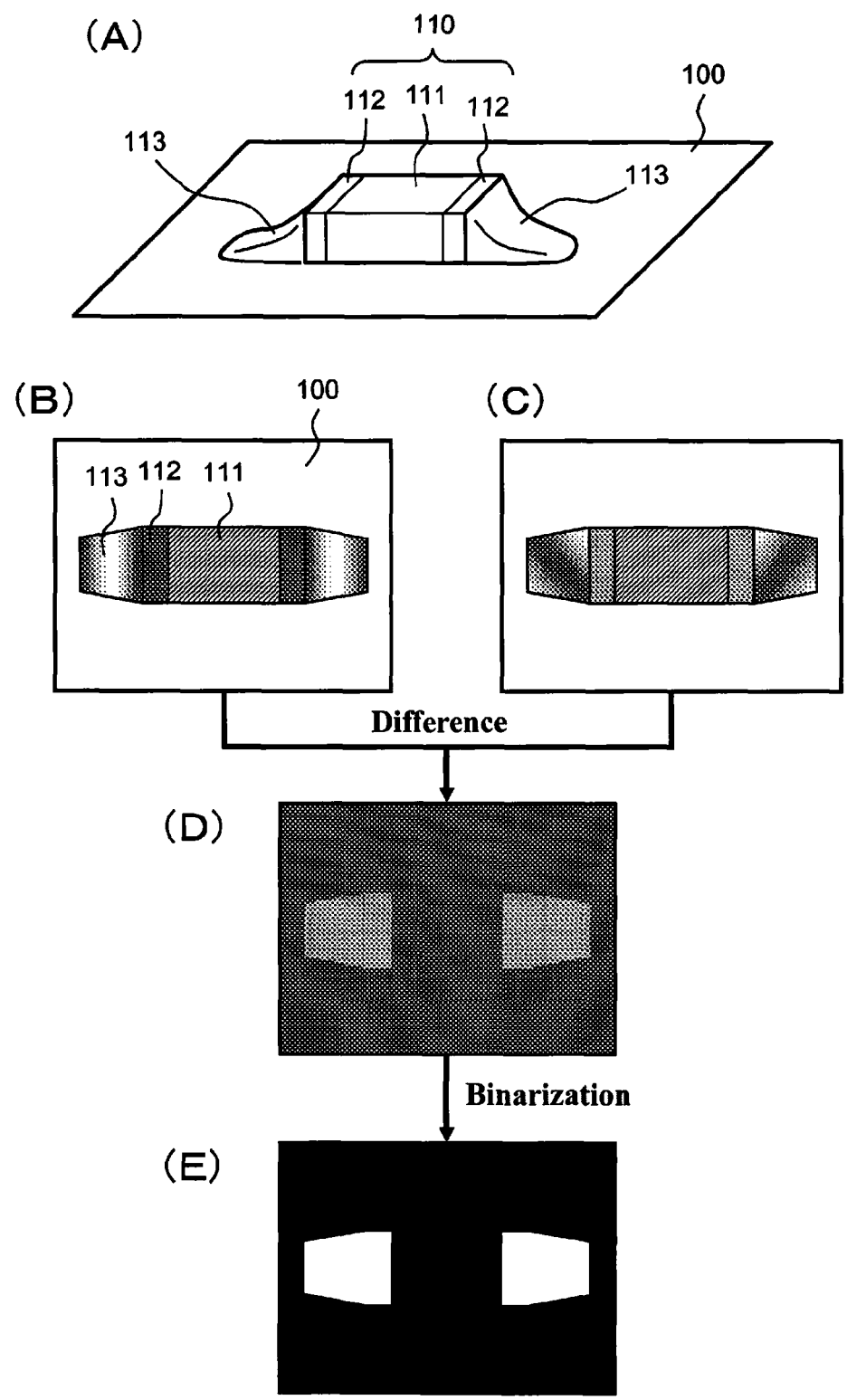
FIG. 9 is a diagram schematically showing an example of a measurement target and images thereof.

Next, the flow of specular object recognition processing will be described, with reference to FIGS. 1, 8 and 9. FIG. 8 is a flowchart of specular object recognition processing, and FIG. 9 schematically shows an example of a measurement target and images thereof. Here, as shown in FIG. 9(A), an example in which a component 110 is mounted on a board 100 is given as the measurement target. The surface of the board 100 and a body 111 of the component 110 are diffuse objects made from resin, and electrodes 112 on either side of the component 110 are specular objects made from metal. Also, the electrodes 112 are soldered with lead-free solder, and these solder portions 113 are specular objects with rough surfaces.

In step S1, the illumination device control unit 66 switches the illumination pattern to the first illumination pattern (upper half of FIG. 7). In step S2, the measurement target 4 is then captured in a state where measurement light of the first illumination pattern is irradiated from the illumination device 3, and data of the first image is acquired. Although not illustrated, the data of the first image obtained here is also utilized in the three-dimensional measurement processing of specular objects.

Next, in step S3, the illumination device control unit 66 switches the illumination pattern to the second illumination pattern (lower half of FIG. 7). In step S4, the measurement target 4 is then captured in a state where measurement light of the second illumination pattern is irradiated from the illumination device 3, and data of the second image is acquired. Note that in the case of performing image capture for each illumination sub-pattern, the processing of steps S1 and S2 and the processing of steps S3 and S4 are each repeated three times.

As shown in FIGS. 9(B) and 9(C), in the first and second images, the color of the objects themselves appears in the case of the board 100 and the component body 111 which are diffuse objects. In contrast, in the case of the electrodes 112 and the solder portions 113 which are specular objects, the color of the illumination which depends on the direction of the normal of the object surface appears rather of the color (metallic color) of the objects themselves, and the color features thereof clearly differ between the first image and the second image.

Next, at step S5, the CPU 60 calculates the difference feature amount F for each pixel of the first image and the second image by the following formula.

$$F=\{abs(r2-r1)/2+(g2-g1)+abs(b2-b1)/2\}/g1$$

Here, r1, g1 and b1 are the values of the channels of the first image, and r2, g2 and b2 are the values of the channels of the second image.

Given that, in the case of specular objects, the values r1, g1, b1, r2, g2 and b2 are generally proportional to the emission intensities R1, G1, B1, R2, G2 and B2 of the illumination, and $$abs(R2-R1)/2+(G2-G1)+abs(B2-B1)/2=100$$

$$G1=150$$

the value of the difference feature amount F in specular object regions will be generally 0.67 (=100/150). On the other hand, given that, in the case of diffuse objects, the values r1, g1, b1, r2, g2 and b2 are generally proportional to the total amounts of light of the illumination, and the illumination is set to satisfy conditions 3 and 4, the value of the difference feature amount F in diffuse object regions will be generally 0. Accordingly, the values of the difference feature amount F are significantly separated between specular object regions and diffuse object regions. FIG. 9(D) shows an image (difference image) of the difference feature amounts F.

At step S6, the CPU 60 binarizes the difference image with a predetermined threshold. The threshold may be a value set in advance (because the difference feature amount F of specular objects will be approximately 0.67 and the difference feature amount F of diffuse objects will be approximately 0, an intermediate value such as 0.5, for example, may be used as the threshold), or may be derived dynamically using Otsu's method of discriminant analysis or the like. FIG. 9(E) shows an exemplary binarized image, the white portions indicating the specular object regions and the black portion indicating the diffuse object region. Specular object regions and diffuse object regions can thus be accurately separated.

Advantages of the Embodiment

According to the visual inspection device of the present embodiment, an image of a measurement target can be separated into specular object regions and diffuse object regions with simple processing that involves comparing two images obtained by capturing the measurement target. Also, because the emission intensity distribution of the illumination patterns are devised such that specular lobe components that are included in reflected light are canceled out, specular object regions can be accurately recognized even in the case of specular objects with rough surfaces or specular objects whose reflection characteristics are not uniform. Furthermore, because the same images are used in both specular object recognition processing and three-dimensional measurement processing, the number of times that imaging is performed can be reduced, and an improvement in the throughput of visual inspection can be achieved.

Note that the above embodiment is intended merely as one specific example of the present invention, and the scope of the present invention should not be construed as being limited to those configurations. The present invention can take various embodiments within the scope of the technical ideas of the invention. For example, although the same images were used in specular object recognition processing and three-dimensional measurement processing in the above embodiment, this need not be the case, and separate images may be captured using illumination patterns suitable for the respective processing. Also, any pattern that satisfies at least conditions 1 and 2 of the above setting conditions may be used as the illumination patterns for use in specular object recognition processing. Also, although the images of three channels were generated using three illumination sub-patterns in the above embodiment, the number of illumination sub-patterns and channels need not be three.

Figure 10:
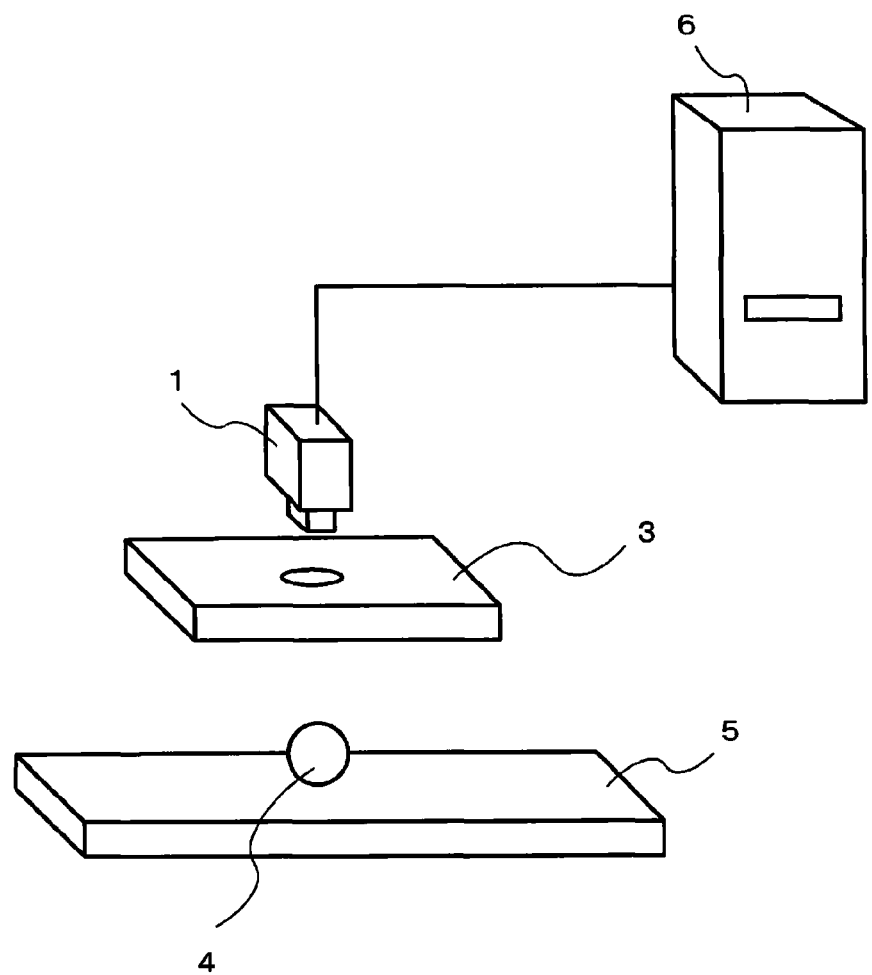
FIG. 10 is a diagram showing the configuration of a visual inspection device that is provided with a plate-like illumination device.
Figure 11:
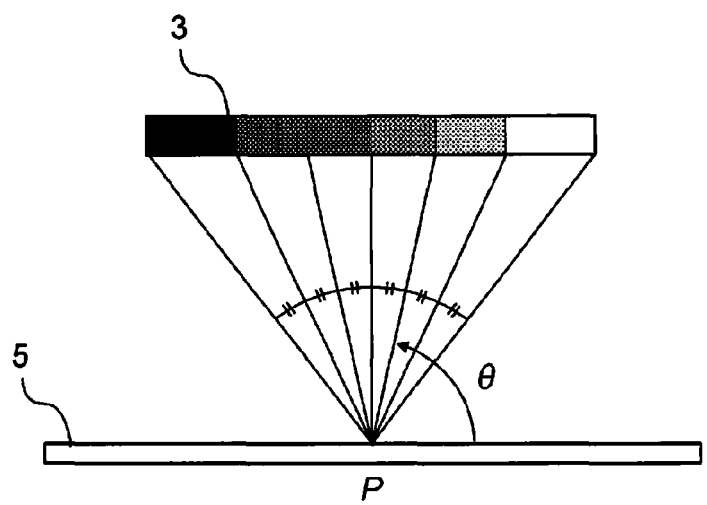
FIG. 11 is a diagram for illustrating an illumination pattern of a plate-like illumination device.

Also, the illumination device 3 is not limited to a dome shape (hemispherical shape), and may have a plate shape such as shown in FIG. 10. Also, the illumination device 3 may have a shape obtained by bending a flat plate into an arc. Specular object regions and diffuse object regions can be divided up, even with illumination device 3 having such shapes, by setting illumination patterns that satisfy the above setting conditions. In the case where the plate-like illumination device 3 is used, the influence of specular lobe can be substantially offset in each pattern by changing the emission intensity linearly relative to an angle θ, as shown in FIG. 11. Here, θ is an angle about a straight line that passes through the point P (point at which the measurement target is placed) and is parallel to the measurement stage 5. Alternatively, θ can also be represented as an angle formed by a plane that passes through the isoemissive intensity lines (isochromatic lines) on the emission region of the illumination device 3 and the point P and a plane parallel to the measurement stage 5.

INDEX TO THE REFERENCE NUMERALS

1 Camera

3 Illumination Device

4 Measurement Target

5 Measurement Stage

6 Information Processing Device h Inspection Head

The invention claimed is:

1. An image processing device comprising:
illumination means having a surface light source for irradiating a measurement target including a specular object and a diffuse object with light of a predetermined illumination pattern;
illumination control means configured to control the illumination pattern of the illumination means;
imaging means configured to image the measurement target; and
region recognition means configured to recognize a specular object region on the measurement target by analyzing an image obtained by the imaging means,
wherein the region recognition means compares a first image obtained by imaging the measurement target in a state where light of a first illumination pattern is irradiated from the illumination means and a second image obtained by imaging the measurement target in a state where light of a second illumination pattern is irradiated from the illumination means, and recognizes the specular object region on the measurement target based on a result of the comparison,
the first image and the second image are images that include a plurality of the same channels,
the first illumination pattern includes a plurality of first illumination sub-patterns that each corresponds to a different one of the plurality of channels, and that have mutually different emission intensity distributions,
one first illumination sub-pattern among the plurality of first illumination sub-patterns has an emission intensity distribution in which an emission intensity is uniform in-plane, and the other first illumination sub-patterns have an emission intensity distribution in which an emission intensity changes linearly in accordance with an angle of incidence of light with respect to the measurement target when considered at a certain cross-section that includes an optical axis of the imaging means,
the second illumination pattern includes a plurality of second illumination sub-patterns that each corresponds to a different one of the plurality of channels, and that have mutually different emission intensity distributions,
the plurality of second illumination sub-patterns all have an emission intensity distribution in which an emission intensity changes linearly in accordance with an angle of incidence of light with respect to the measurement target when considered at a certain cross-section that includes the optical axis of the imaging means, and
each first illumination sub-pattern and second illumination sub-pattern corresponding to the same channel have mutually different emission intensity distributions.

2. The image processing device according to claim 1, wherein the region recognition means derives a feature amount representing a difference between the first image and the second image, using a value obtained by dividing a value of all the channels of the first image and the second image by a value of the channel corresponding to the first illumination sub-pattern, in the first image, having the emission intensity distribution in which the emission intensity is uniform in-plane.

3. The image processing device according to claim 1, wherein a ratio of a total amount of light in-plane between the plurality of first illumination sub-patterns constituting the first illumination pattern is equal to a ratio of the total amount of light in-plane between the plurality of second illumination sub-patterns constituting the second illumination pattern.

4. The image processing device according to claim 1, wherein each first illumination sub-pattern and second illumination sub-pattern corresponding to the same channel have total amounts of light in-plane that are equal to each other.

5. The image processing device according to claim 1, wherein the emission intensity distribution of each first illumination sub-pattern and the emission intensity distribution of each second illumination sub-pattern are set so as to satisfy $$\{L1_1(q), \ldots, L1_n(q)\} \neq \{L2_1(q), \ldots, L2_n(q)\}$$

for all points q, where
q is a point on the surface light source of the illumination means,
i is a channel (i=1, ..., n; n is an integer of 2 or more),
$L1_i(q)$ is the emission intensity at the point q of the first illumination sub-pattern corresponding to the channel i, and
$L2_i(q)$ is the emission intensity at the point q of the second illumination sub-pattern corresponding to the channel i.

6. The image processing device according to claim 1, wherein the emission intensity distribution of each first illumination sub-pattern and the emission intensity distribution of each second illumination sub-pattern are set such that $$f1(L1_1(q)-L2_1(q)) + \ldots + fn(L1_n(q)-L2_n(q))$$

takes the same value for all points q, where
q is a point on the surface light source of the illumination means,
i is a channel (i=1, ..., n; n is an integer of 2 or more),
$L1_i(q)$ is the emission intensity at the point q of the first illumination sub-pattern corresponding to the channel i,
$L2_i(q)$ is the emission intensity at the point q of the second illumination sub-pattern corresponding to the channel i, and
fi is a function determined in advance for each channel i.

7. The image processing device according to claim 6, wherein the first illumination sub-pattern corresponding to a channel k (1≤k≤n) has an emission intensity that is uniform in-plane, and
the region recognition means derives a feature amount representing a difference of the first image and the second image relating to the point p using a value that is obtained by dividing $$f1(V1_1(p)-V2_1(p)) + \ldots + fn(V1_n(p)-V2_n(p))$$

by a value of $V1_k(p)$
where p is a point on the measurement target,
$V1_i(p)$ is the value of the channel i of the pixel corresponding to the point p in the first image, and
$V2_i(p)$ is the value of the channel i of the pixel corresponding to the point p in the second image, and
the region recognition means determines that a portion at the point p is a specular object if the feature amount is greater than a threshold.

8. The image processing device according to claim 1, further comprising:
three-dimensional measurement processing means configured to compute a direction of a normal of a surface of the specular object on the measurement target, by analyzing an image obtained by the imaging means, and configured to compute a three-dimensional shape of the surface of the specular object from a result of the direction computation, wherein the first image is also utilized in computing the three-dimensional shape by the three-dimensional measurement processing means.

9. A method for controlling an image processing device having illumination means having a surface light source for irradiating a measurement target including a specular object and a diffuse object with light of a predetermined illumination pattern, illumination control means configured to control the illumination pattern of the illumination means, and region recognition means configured to recognize a specular object region on the measurement target by analyzing an image obtained by the imaging means, the method comprising the steps of:

acquiring a first image by imaging the measurement target using the imaging means, in a state where light of a first illumination pattern is irradiated from the illumination means;

acquiring a second image by imaging the measurement target using the imaging means, in a state where light of a second illumination pattern is irradiated from the illumination means; and recognizing a specular object region on the measurement target based on a result of a comparison between the first image and the second image by the region recognition means, wherein the first image and the second image are images that include a plurality of the same channels, the first illumination pattern includes a plurality of first illumination sub-patterns that each corresponds to a different one of the plurality of channels, and that have mutually different emission intensity distributions, one first illumination sub-pattern among the plurality of first illumination sub-patterns has an emission intensity distribution in which an emission intensity is uniform in-plane, and the other first illumination sub-patterns have an emission intensity distribution in which an emission intensity changes linearly in accordance with an angle of incidence of light with respect to the measurement target when considered at a certain cross-section that includes an optical axis of the imaging means, the second illumination pattern includes a plurality of second illumination sub-patterns that each corresponds to a different one of the plurality of channels, and that have mutually different emission intensity distributions, the plurality of second illumination sub-patterns all have an emission intensity distribution in which an emission intensity changes linearly in accordance with an angle of incidence of light with respect to the measurement target when considered at a certain cross-section that includes the optical axis of the imaging means, and each first illumination sub-pattern and second illumination sub-pattern corresponding to the same channel have mutually different emission intensity distributions.

10. The method for controlling an image processing device according to claim 9, wherein the region recognition means derives a feature amount representing a difference between the first image and the second image, using a value obtained by dividing a value of all the channels of the first image and the second image by a value of the channel corresponding to the first illumination sub-pattern, in the first image, having the emission intensity distribution in which the emission intensity is uniform in-plane.

11. A non-transitory computer-readable medium storing computer executable instructions that when executed by a computer cause an image processing device to execute the steps of the method for controlling an image processing device according to claim 10.

12. An inspection system comprising:

illumination means having a surface light source for irradiating a measurement target including a specular object and a diffuse object with light of a predetermined illumination pattern;

illumination control means configured to control the illumination pattern of the illumination means;

imaging means configured to image the measurement target;

region recognition means configured to recognize a specular object region on the measurement target by analyzing an image obtained by the imaging means; and inspection means configured to extract an image of the specular object region from the image obtained by the imaging means and inspecting the extracted image, wherein the region recognition means compares a first image obtained by imaging the measurement target in a state where light of a first illumination pattern is irradiated from the illumination means and a second image obtained by imaging the measurement target in a state where light of a second illumination pattern is irradiated from the illumination means, and recognizes the specular object region on the measurement target based on a result of the comparison, the first image and the second image are images that include a plurality of the same channels, the first illumination pattern includes a plurality of first illumination sub-patterns that each corresponds to a different one of the plurality of channels, and that have mutually different emission intensity distributions, one first illumination sub-pattern among the plurality of first illumination sub-patterns has an emission intensity distribution in which an emission intensity is uniform in-plane, and the other first illumination sub-patterns have an emission intensity distribution in which an emission intensity changes linearly in accordance with an angle of incidence of light with respect to the measurement target when considered at a certain cross-section that includes an optical axis of the imaging means, the second illumination pattern includes a plurality of second illumination sub-patterns that each corresponds to a different one of the plurality of channels, and that have mutually different emission intensity distributions, the plurality of second illumination sub-patterns all have an emission intensity distribution in which an emission intensity changes linearly in accordance with an angle of incidence of light with respect to the measurement target when considered at a certain cross-section that includes the optical axis of the imaging means, and each first illumination sub-pattern and second illumination sub-pattern corresponding to the same channel have mutually different emission intensity distributions.

13. The inspection system according to claim 12, wherein the region recognition means derives a feature amount representing a difference between the first image and the second image, using a value obtained by dividing a value of all the channels of the first image and the second image by a value of the channel corresponding to the first illumination sub-pattern, in the first image, having the emission intensity distribution in which the emission intensity is uniform in-plane.

* * * * *